United States Patent [19]
Filangeri

[11] Patent Number: 6,093,146
[45] Date of Patent: Jul. 25, 2000

[54] PHYSIOLOGICAL MONITORING

[75] Inventor: Edward M. Filangeri, Santa Clara, Calif.

[73] Assignee: Matsushita Electric Works, Ltd., Japan

[21] Appl. No.: 09/092,584

[22] Filed: Jun. 5, 1998

[51] Int. Cl.$^7$ ..................................................... A61B 5/00

[52] U.S. Cl. ...................... 600/300; 128/904; 379/106.2

[58] Field of Search ........................... 128/904, 897–898; 600/300–301, 481–500; 379/106.2, 106.1–106.11

[56] References Cited

U.S. PATENT DOCUMENTS

| | | | |
|---|---|---|---|
| 3,882,277 | 5/1975 | DePedro et al. | 179/2 |
| 3,986,498 | 10/1976 | Lewis | 128/2.06 R |
| 4,173,971 | 11/1979 | Karz | 128/702 |
| 4,531,527 | 7/1985 | Reinhold, Jr. et al. | 128/696 |
| 4,608,994 | 9/1986 | Ozawa et al. | 128/670 |
| 4,712,562 | 12/1987 | Ohayon et al. | 128/672 |
| 4,751,726 | 6/1988 | Hepp et al. | 379/106.02 |
| 4,827,943 | 5/1989 | Bornn et al. | 128/668 |
| 4,830,018 | 5/1989 | Treatch | 128/677 |
| 4,889,134 | 12/1989 | Greenwold et al. | 128/696 |
| 5,012,411 | 4/1991 | Policastro et al. | 364/413.06 |
| 5,224,485 | 7/1993 | Powers et al. | 128/696 |
| 5,284,151 | 2/1994 | Onoda | 128/710 |
| 5,313,953 | 5/1994 | Yomtov et al. | 128/696 |
| 5,411,031 | 5/1995 | Yomtov | 128/706 |
| 5,522,396 | 6/1996 | Langer et al. | 128/696 |
| 5,544,661 | 8/1996 | Davis et al. | 128/700 |
| 5,606,978 | 3/1997 | Armstrong et al. | 128/711 |
| 5,617,871 | 4/1997 | Burrows | 128/696 |
| 5,645,068 | 7/1997 | Mezack et al. | 128/670 |
| 5,694,940 | 12/1997 | Unger et al. | 128/696 |
| 5,751,797 | 5/1998 | Saadeh | 379/106.3 |
| 5,787,155 | 7/1998 | Luna | 379/106.2 |

OTHER PUBLICATIONS

Brentwood, "EZ Scan Digital Recorder," product information, 1 pg., downloaded from WWW. on Jan. 29, 1998.

Biosensor Corp., "Biosensor Products," products information, 4 pgs., 1997, downloaded from WWW. on Jan. 28, 1998.

Protocol, "Protocol Cordless (TM)," product information, 1 pg., downloaded from WWW. on Jan. 28, 1998.

Spacelabs Medical, Inc., "Patient Monitoring ProductsAdult Critical Care," product information, 3.pgs., 1997, downloaded from WWW. on Jan. 28, 1998.

Critikon, a Division of Johnson & Johnson Medical, Inc., "Observer Central Station," product information, 3 pgs., Jan. 17, 1998, downloaded from WWW. on Jan. 28, 1998.

Hewlett–Packard Co., HP Digital Telemtry System (M1403A), Healthcare Monitoring & Info Systems, 1997, 2 pgs., downloaded from WWW. on Jan. 28, 1998.

CSI Systems, "Criticare Vital Signs Systems," product information, 4 pgs., downloaded from WWW. on Jan. 28, 1998.

(List continued on next page.)

*Primary Examiner*—Max Hindenburg
*Assistant Examiner*—Michael Astorino
*Attorney, Agent, or Firm*—Fish & Richardson P.C.

[57] ABSTRACT

A physiological monitoring system includes a base station, the base station having a first wireless transceiver, and a patient monitor, the patient monitor comprising a data input, the data input configured to receive data regarding a physiological condition of a patient, the patient monitor further including a second wireless transceiver, the patient monitor capable of entering a wireless communications link with the base station through the first and second wireless transceivers, and of transmitting in substantially real-time the received data from the patient to the base station, the patient monitor further including a controller and a memory, the controller being configured to store in the memory the received data when the wireless communications link is interrupted.

29 Claims, 9 Drawing Sheets

OTHER PUBLICATIONS

Marquette Medical Systems, "IMPACT.wf Paging System," product information, 4 pgs., 1997, downloaded from WWW. on Jan. 28, 1998.

Marquette Medical Systems, "SEER XT Ambulatory Digital Analysis Recorders," product information, 6 pgs., 1997, downloaded from WWW. on Jan. 28, 1998.

Marquette Medical Systems, "CD Telemetry," product information, 5 pgs., 1997, downloaded from WWW. on Jan. 28, 1998.

Marquette Medical Systems, "Transmitter APEX S," product information, 4 pgs., 1997, downloaded from WWW. on Jan. 27, 1998.

Marquette Medical Systems, "MARS 8000," product information, 5 pgs., 1997, downloaded from WWW. on Jan. 27, 1998.

Marquette Medical System, CD Telemetry–LAN, product information, 2 pgs., 1997, downloaded from WWW. on Jan. 27, 1998.

PHYSIOLOGICAL MONITORING

BACKGROUND

This invention relates to physiological monitoring of organisms, including human patients.

Patients receiving health care often require physiological measurements to be taken over relatively long periods of time. These measurements can be relatively easily taken when a patient is localized, for example during a hospital stay. In those instances, the patient can be connected to physiological monitors directly coupled to central stations that monitor and record patient data such as heart rate, breathing rates, blood pressure, ECG and EEG signals, and blood chemistry information.

Often patients require such physiological monitoring at home, away from a hospital setting. Holter monitoring is often used to perform such measurements. With Holter monitoring, the patient wears a portable data recorder that makes a tape recording of continuous physiological data such as from an ECG or EEG. Usually the Holter monitoring unit is unobtrusive enough so that the patient can perform usual day-to-day activities with little discomfort or encumbrance. Periodically, the patient must return the unit with its data to the doctor or technician to download and review the recorded data. Sometimes the lag from data recording to data review can be too long in relation to the relative urgency of the patient's condition. Additionally, having to return the recorded tapes can be inconvenient when multiple recordings are necessary. Many Holter monitoring units now use digital storage systems such as removable flash memory cards and the like.

Recently, real-time remote physiological monitors have been developed. Such real-time monitors typically include a portable monitoring unit worn by the patient, a base station that communicates with the portable unit, and a central data collection station. The portable unit performs the physiological measurements in a manner similar to a Holter unit, but instead of making a self-contained recording, transmits the data to the base station via a wireless link (e.g., by RF or IR transmission). The base station is located somewhere near the patient. As the base station receives the real-time data, it simultaneously retransmits it to a central station via a communication link, typically the public telephone system. This real-time form of physiological monitoring allows data to be sent from patient to care giver within a matter of seconds. This allows for a faster diagnosis and a quicker response to emergencies relative to traditional Holter monitoring.

SUMMARY

In general, in one aspect, the invention features a physiological monitoring system including a base station, the base station having a first wireless transceiver, and a patient monitor, the patient monitor comprising a data input, the data input configured to receive data regarding a physiological condition of a patient, the patient monitor further comprising a second wireless transceiver, the patient monitor capable of entering a wireless communications link with the base station through the first and second wireless transceivers, and of transmitting in substantially real-time the received data from the patient to the base station, the patient monitor further comprising a controller and a memory, the controller being configured to store the received data in the memory when the wireless communications link is interrupted.

Embodiments of the invention may include one or more of the following features. The controller can be further configured to end the storing of the received data and to send to the base station the stored received data from the memory combined with new received data received through the data input, when the wireless communications link is reestablished. The stored received data can be combined with the new received data in an interleaved fashion. A central station can be coupled by a communications link to the base station, and the communications link can be formed over a telephone network.

The base station can include a base station memory and a modem link, and can also include a base station controller, the base station controller configured to store in the base station memory received data from the patient monitor when the communications link with the central station is interrupted. The base station controller can be further configured to end the storing of the received data from the patient monitor and to send to the central station the stored received data from the base station memory combined with new received data received through the patient monitor, when the communications link is reestablished. The stored received data can be combined with the new received data from the patient monitor in an interleaved fashion. The central station can organize the combined stored received data and the new received data into a substantially continuous, time ordered data record. The communications link can be interrupted when a telephone connected to the base station is used to make a telephone call, or receives an incoming telephone call. The base station controller can be further configured to end the storing of the received data from the patient monitor and to send to the central station the stored received data from the base station memory combined with new received data received through the patient monitor, when the telephone call ends.

In general, in another aspect, the invention features a method for physiological monitoring including receiving, at a patient monitor, data regarding a physiological condition of a patient, transmitting in substantially real-time the received data from the patient to a base station via a wireless communications link, and storing in memory of the patient monitor the received data when the wireless communications link is interrupted.

Advantages of the invention may include one or more of the following. The portable patient unit provides for local memory storage of physiological data whenever the communication link between patient and base station is broken. The base station provides for memory storage of the data whenever its communication link between it and the central station is broken. Provision of this memory storage ensures that very little if any data will be lost, and allows for a patient to move with ease into and out of range of the base station, assured that the patient's data will remain relatively secure. Furthermore, whenever any of the communication links are restored, the invention provides for concurrent transmission of both stored and current data which can be spliced together into a seamless data stream at either the base station or the central station. Also, memory storage of data can automatically begin whenever a phone coupled to the phone line used by the base station is used, and the data transmission can resume whenever such phone use ends. A patient does not need an extra dedicated phone line to have continual physiological monitoring, and the patient is allowed greater freedom of movement away from a base station without loss of data. Further, since the patient unit typically has non-volatile memory, it can also be used as a simple Holter-type monitor, providing a flexible monitoring system.

Other features and advantages of the invention will become apparent from the following description and from the claims.

DRAWINGS

DESCRIPTION

Figure 1:
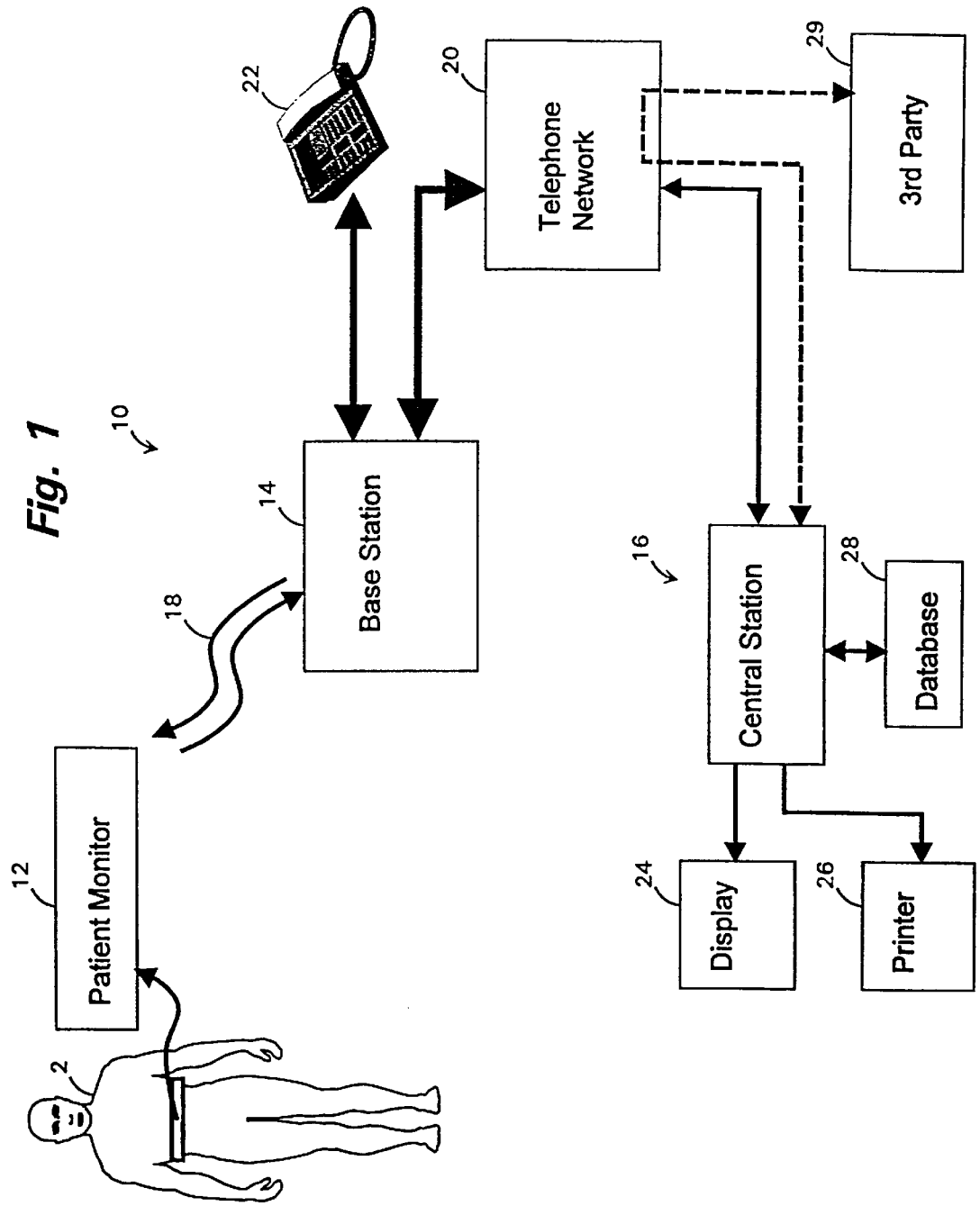
FIG. 1 is schematic diagram of a physiological monitoring system.

Referring to FIG. 1, a physiological monitoring system 10 includes a patient monitor 12 worn by a patient 2 (which can be, for example, a human being, or an animal under veterinary care), a base station 14, and a central station 16. Patient monitor 12 and base station 14 communicate via, for example, a wireless communication link 18, such as a radio frequency (RF) or infrared (IR) communication system. Base station 14 is coupled to an external communication network 20, typically a public telephone network, and to one or more telephones 22. Central station 16 typically includes a display system 24 (for example, a computer monitor), printing device 26, and database system 28.

Figure 2:
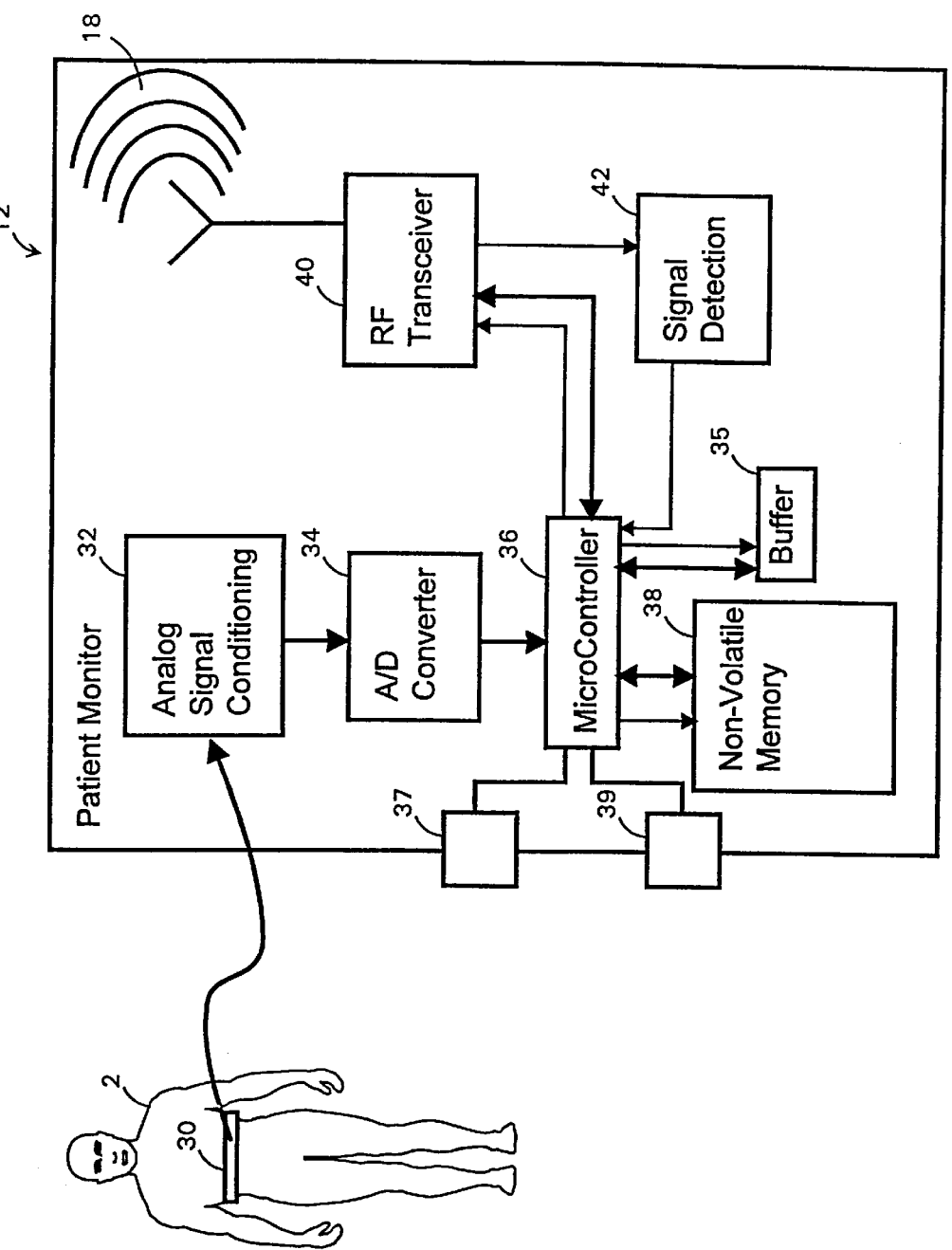
FIG. 2 is a schematic diagram of a patient monitor.

Referring to FIG. 2, patient 2 is physically coupled to patient monitor 12 via coupling 30. Physiological signals such as ECG, blood pressure, temperature, or respiration are filtered and amplified by an analog signal conditioning block 32, and then converted to digital signals by an analog-to-digital (A/D) converter 34. The digitized data is then transmitted by micro-controller 36 to base station 14 through RF transceiver 40 via wireless communication link 18. This constitutes a Normal Transmit Mode. When the data signals are not being transmitted, micro-controller 36 can store them in non-volatile memory 38, which can be conventional flash memory. Microcontroller 36 is coupled to RF transceiver 40 via an asynchronous serial link at approximately 19.2 Kbaud, however any number of data communication links can be used.

Micro-controller 36 can be a Motorola MC68HC711K4 single-chip microcomputer, operating with a bus speed of 2 MHz. Non-volatile memory 38 can be AMD AM29F040 512k×8 Flash memory. With an A/D sampling of data of 100 samples/sec, with 8 bits per sample, patient monitor 12 can store approximately 88 minutes of patient data. Patient monitor 12 can be powered by rechargeable batteries, e.g., by four AA-size Lithium Metal batteries made by Tadiran Industries, allowing for 24 hours continuous operation.

Signal detector 42 monitors the status of RF transceiver 40 to detect when wireless communication link 18 becomes unstable or is severed, at which time signal detector 42 indicates to micro-controller 36 to enter a Wireless Fault Induced Memory Mode. During this mode, caused for example when the patient monitor 12 leaves the communication range of base station 14, patient monitor 12 temporarily stops transmitting data and starts storing data sequentially in non-volatile memory 38. During the Wireless Fault Induced Memory Mode, patient monitor 12 enters a low power state and periodically powers up to determine whether the wireless communication link 18 can be reestablished. If link 18 is reestablished, patient monitor 12 reenters Normal Transmit Mode and resumes transmitting real-time data. Concurrently, patient monitor 12 transmits the recorded data from non-volatile memory 38. Real-time data is transmitted in discrete bursts (described further below). Between each burst of real-time data, patient monitor 12 can transmit one or more bursts of recorded data from memory 38 until a new burst of real-time data is ready for transmission. The entire contents of local memory 38 are thereby transmitted in this interlaced manner. Both real-time and recorded data can then be transmitted from base station 14 to central station 18. Since each data burst (whether stored or realtime) is uniquely time stamped, central station 16 can correctly splice the recorded data stream with the real-time stream to produce a single, continuous data stream.

Patient monitor 12 can also be configured by signals from the base station or central station via wireless communication link 18. Signal detector 42 can determine if such configuration information (including, for example, channel montage, where different channels are assigned to different data streams: e.g., channel 1 is ECG1, channel 2 is ECG2, channel 3 is the temperature) has been received by RF transceiver 40. Either signal detector 42 can then signal the micro controller 36 to pause data transmission and receive the incoming configuration information instead. During this process, outgoing data from patient 2 can be stored in non-volatile memory 38, or in buffer 35, and then sent when incoming data stops. Or, incoming data can be received between bursts of outgoing data, resulting in no data delays. To facilitate these data paths, RF transceiver 40 can also be configured for half or full duplex operation. Furthermore, RF transceiver 40 can have an internal memory buffer that can be used in tandem with other buffers 35 (located, e.g., in a separate RAM or in an internal buffer in microcontroller 36) to store data before transmission. This data can include, for example, the last few seconds of transmitted data to ensure that data transmitted at the onset of a communication interruption is not lost.

Patient monitor 12 can also include a direct connector 39 for coupling patient monitor 12 to base station 14 through cabling instead of RF transmissions. In addition, patient monitor 12 can include a patient event monitor 37 explained further below.

Figure 3:
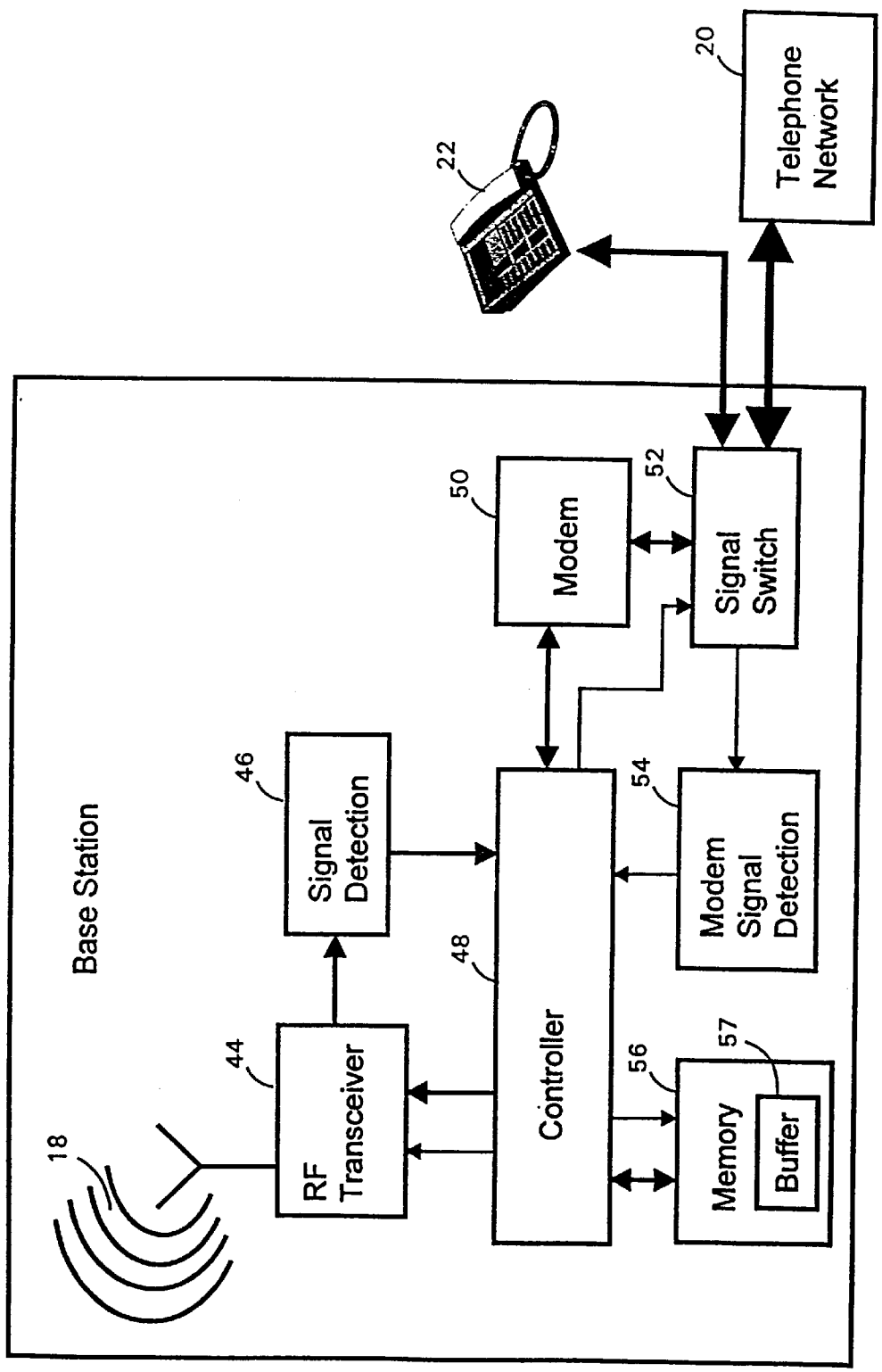
FIG. 3 is a schematic diagram of a base station.

Referring to FIG. 3, base station 14 typically includes RF transceiver 44, signal detector 46, controller 48, modem 50, signal switch 52, signal detector 54 and memory 56. RF transceiver 44 is coupled via wireless communication link 18 to the corresponding RF transceiver 40 in patient monitor 12. Base station 14 when located in the vicinity of patient 2 and patient monitor 12 typically maintains a stable RF link. Base station 14 can also comprise a series of RF transceivers (or other communication link transceivers) located, e.g., through a series of rooms, so that patient monitor 12 can be in continual contact as patient 2 moves about.

In Normal Transmit Mode, RF transceiver 44 receives data from patient monitor 12, and controller 48 directs the data through modem 50 and signal switch 52 onto telephone network 20 (and then on to central station 16). In Normal Transmit Mode, signal switch 52 is set so that modem 50 is coupled to, and telephone 22 is uncoupled from, public network 20. One embodiment transmits about 6–7 seconds of physiological data in a single 300 ms data burst from patient monitor 12 to base station 14. This helps to minimize power consumption, particularly at RF transceiver 40.

Base station 14 typically expects data transmissions from patient monitor 12 at regular intervals (e.g., every 6 to 7 seconds). If RF signal detection unit 46 does not detect new data from patient monitor 12 before a specified timeout occurs (e.g., 100 milliseconds after the normal 6 or 7 second period between bursts), or patient monitor 12 continues to send error-filled data bursts, base station 14 enters a Wireless Fault Induced Memory Mode and signals central station 16 via modem 50 that this condition has occurred. In this mode, RF transceiver 44 continues to send a linking signal to central station 16 until patient monitor 12 successfully re-links with base station 14 and resumes data transmission. Patient monitor 12 will continue to attempt to resynchronize with base station 14 for typically 6 seconds every minute. This intermittent synchronization is used to conserve battery energy, since transceiver 40 of patient monitor 12 consumes far more energy attempting to synchronize than during normal transmission. Average synchronization requires, e.g., about 4 seconds, so that allowing 6 seconds to attempt connection should be adequate. When base station 14 once again receives data from patient monitor 12 with no detectable (uncorrectable) errors, it then resumes normal transmit mode and so signals central station 16 via modem 50.

If modem signal detection block 54 detects that the telephone 22 has been taken off the hook (e.g., because patient 2 is making a telephone call), base station 14 Enters Modem Fault Induced Memory Mode and so signals central station 16 via modem 50. After signaling central station 16, signal switch 52 disconnects modem 50 from public telephone network 20 and connects telephone 22 so that the patient can complete the telephone call. During Modem Fault Induced Memory Mode, wireless communication link 18 will be maintained so that data continues transmitting from patient monitor 12 to base station 14. During Modem Fault Induced Memory Mode, this data is rerouted to base station memory 56 where it is sequentially stored until the system returns to Normal Transmit Mode. When modem signal detection block 46 detects that patient 2 has hung up telephone 22, signal switch 52 reconnects modem 50 to public telephone network 20, and the modem link to central station 16 is reestablished. The system thus reenters Normal Transmit Mode and resumes transmitting real-time data to central station 16 while concurrently transmitting recorded data from base station memory 56. Again, central station 16 can then splice the recorded data stream into the real-time stream to produce a single continuous uninterrupted data stream.

If the patient's local telephone service includes a "call waiting" feature, then system 10 can also allow the patient to receive incoming telephone calls. If modem signal detection block 54 detects that there is an incoming telephone call from public telephone network 20, then base station 14 can enter Modem Fault Induced Memory Mode and signal central station 16 that this condition has occurred. Just as with a patient-initiated telephone call described above, signal switch 52 can then disconnect modem 50 from telephone network 20, connect telephone 22 to telephone network 20, and then switch the active line from the link with central station 16 to the incoming caller. When modem signal detection block 54 detects that the patient has hung up telephone 22, the system returns to Normal Transmit Mode just as in the case when the patient initiates and then terminates a telephone call.

It may be that a fault in telephone network 20 itself might cause a communication failure with central station 16, and with such an occurrence, some data might be lost, since base station 14 will believe it was correctly sent during the early stage of disruption. To make system 10 more tolerant of this sort of fault, a buffer 57 formed in RAM memory 56 can store the last few seconds of data sent to central station 16, and allow such data to be resent in the event of this sort of network fault. When base station 14 does not receive receipt confirmation from central station 16 for a particular transmitted data block, base station 14 can resend it from its buffer 57.

Figure 4:
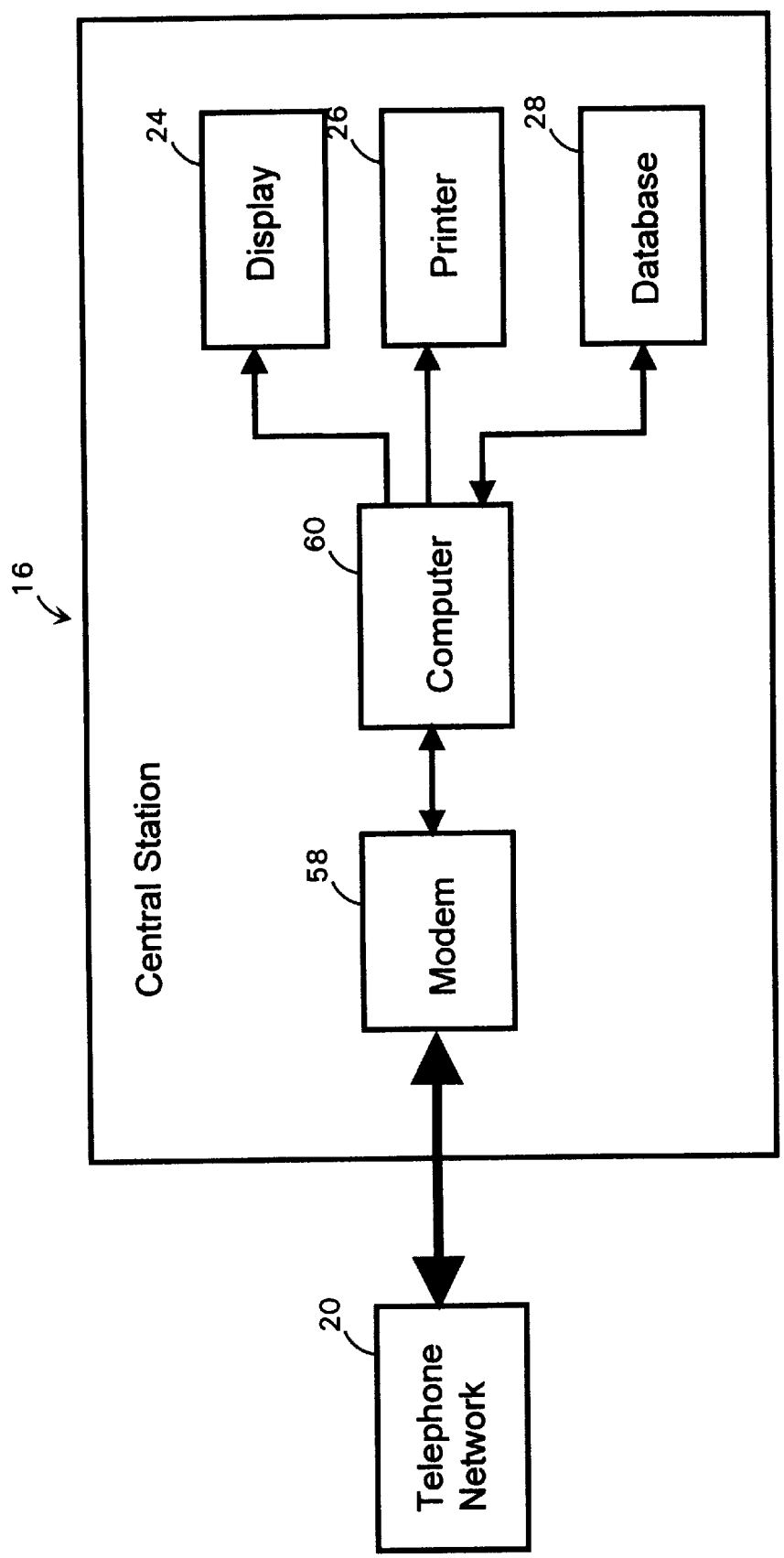
FIG. 4 is a schematic diagram of a central station.

Referring to FIG. 4, central station 16 includes modem 58, computer 60, display 24, printer 26, and database 28. Central station 16 is typically located remote from base station 14 and patient monitor 12—it can be in the same building, or many miles away. Modem 58 is coupled to public telephone network 20, and receives and transmits data to and from base station 14. As central station 16 receives data, it can be displayed on display 24, printed out on printer 26, stored in database 28, or retransmitted to a third party (such as a patient's physician). Multiple stored and received data records can be reviewed and compared. Computer 60 can also contain an expert system that performs real-time or delayed analysis of received patient data. Such a system can automatically generate analysis reports, or activate alarms if emergency conditions occur. The alarms can be audible or shown on display 24. The reports can also be forwarded to a third party, e.g., a physician. Additionally, if an emergency condition occurs, computer 60 can automatically send a message via modem 58 and telephone network 20 to, e.g., a pager of a clinician on call for the patient.

Figure 5:
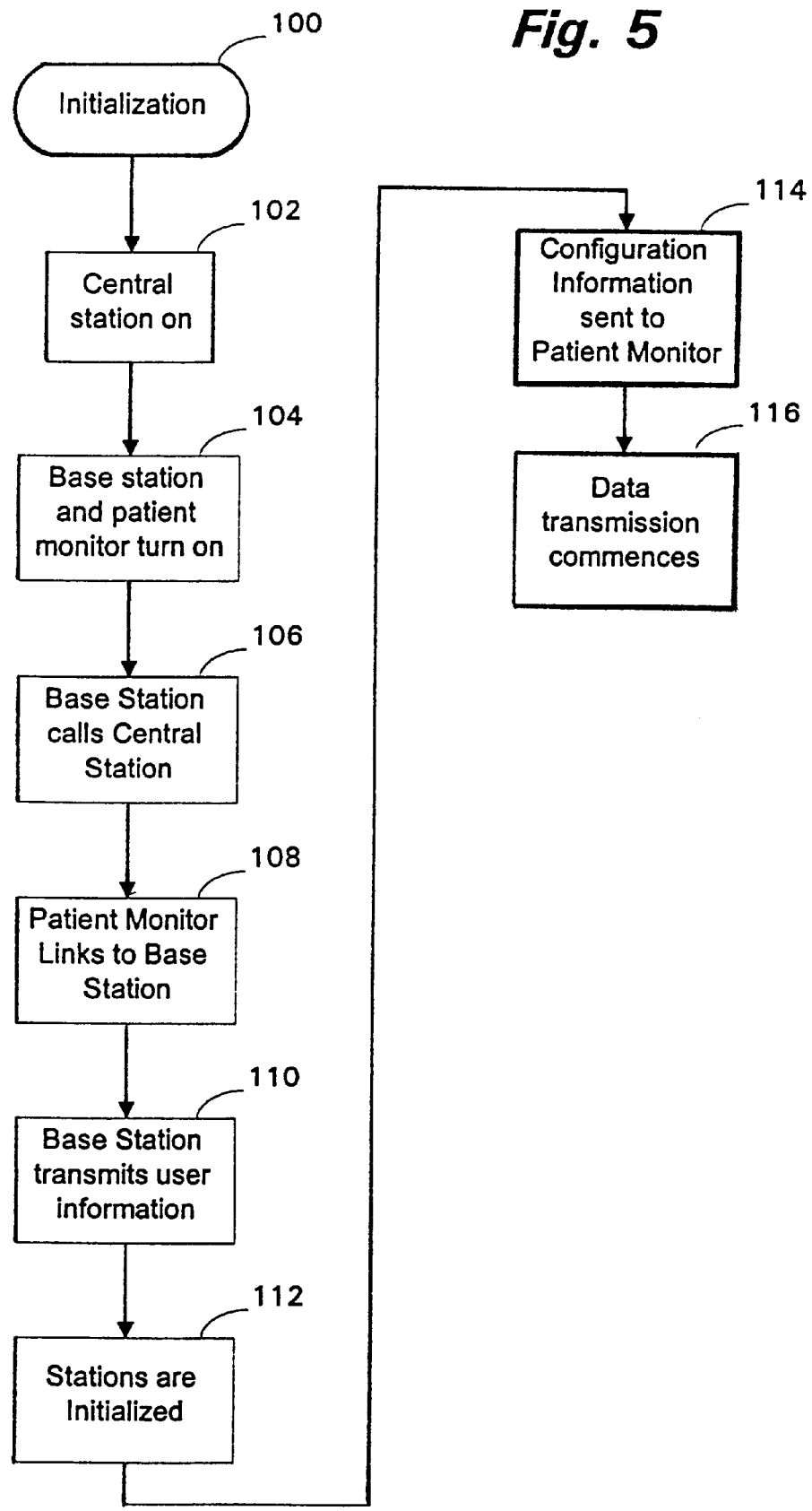
FIG. 5 is a flow chart of an initialization of a physiological monitoring system.

Referring to FIG. 5, initialization 100 of physiological monitoring system 10 begins when central station 16 is typically left in an "on" state (step 102), ready to receive remote telephone calls from base stations 14. When patient 2 is ready to have physiological data recorded and sent to central station 16, patient 2 typically turns on both base station 14 and patient monitor 12, and appropriately attaches any required physiological monitoring equipment from patient monitor 12 to his or her body (step 104). Next, base station 14 calls central station 16 over public telephone network 20 (step 106). This calling step can also be over a private network, for example, within a medical complex or hospital. Patient monitor 12 synchronizes via wireless communication link 18 to base station 14 (step 108). Base station 14 also transmits user information such as name, address, patient ID, attending physician, medical condition, and the like (step 110). This information can be located at either patient monitor 12 or base station 14.

In one embodiment, wireless communication link 18 employs a frequency hopping, spread spectrum RF communication system, using WIT2400 2.4 Ghz wireless transceivers from Digital Wireless Corporation. The frequency hopping scheme has desirable resistance to narrowband interference and fading, and also provides a measure of data security. Noise immunity can be particularly useful with regard to medical devices operating in the ISM RF bands, since there may be one or more relatively high-power narrowband interference sources within the field of coverage of patient monitor 12.

The WIT2400 RF transceiver 40 in patient monitor 12 is configured as a remote unit, and when activated, attempts to synchronize to the frequency hopping pattern of companion RF transceiver 44 of base station 14. When the two RF transceivers 40 and 44 synchronize, data transmission can begin.

When found by transceiver 44 of base station 14, patient monitor 12 transmits an initialization code to "zero out" the time base, and tell the system that a new data record is starting (step 108). This initialization sequence differentiates the power-up condition from a loss-of-signal condition. The initialization code can be as simple as a 00:00 time stamp, and is, in turn, propagated to central station 16 (step 112). Central station 16 then transmits configuration information (such as channel gain and channel montage) through base station 14 to patient monitor 12 (step 114). System 10 is then ready to receive data from patient monitor 12 (step 116).

One data gathering and transmission protocol for, e.g., electrocardiogram (ECG) data, uses data sampled at 120 samples per second. At the highest protocol level, the data is divided into bursts, whereby a buffer within patient monitor 12 (which, as mentioned above, can be RAM buffer 35, or a buffer in RF transceiver 40 or in microcontroller 36 or another buffer system) stores approximately 5 seconds of data. When the buffer is full, its contents are transmitted to WIT2400 RF transceiver 40 at 19.2 kbaud via a hardwired serial port. The data is then transmitted via RF communications link 18 from patient monitor 12 to base station 14 at approximately 250 kbaud.

The first four bytes of each burst of data is a time stamp. The time stamp has a 4 millisecond resolution and counts relative from initialization. The data with the time stamps are propagated to central station 16 which monitors the activities taking place throughout system 10.

The data has a single byte of resolution (but can have, with greater data throughput, higher resolution). Data beginning with FFh is reserved for special codes, providing a resolution of 255 discrete levels. When central station 16 encounters an FFh byte ("h" for hexadecimal), it reads the subsequent bytes to determine the nature of the special code. Example codes include:

| | |
|---|---|
| FF00h | End of Burst |
| FF55h | Patient Event Button |
| FFAAxxh [00-FEh] | Battery level |
| FFFFh | End of transmission |

Each data burst will always be terminated by "FF00h". A patient event button 37 can be located on patient monitor 12 and pushed by the patient 2 at any time during the transmission, to tag a particular string of data as occurring at some point in time pertinent to patient 2 (e.g., during angina or racing heart beat, or to mark an exercise period or other activity). A visual and audible alert can be activated at base station 14 when patient event button 37 is depressed. The battery level of patient monitor 12 can be transmitted to central station 16 on a regular schedule or in response to polling by central station 16. When patient monitor is powered down, it sends the "end of transmission" code.

All downstream communications (such as those from central station 16 to base station 14 or patient monitor 12) occur between data bursts. Such communications can include sending configuration information and polling patient monitor 12 for its battery level.

At a lower protocol level, the communication between WIT2400 transceivers is in a packetized data format of between 0 and 255 bytes. The format has a start character (such as 02h), followed by a remote address comprising a unique byte-long address of the patient monitor. This allows several patient monitors 12 to be used simultaneously with one base station 14. Remote address is followed by a length indication for the packet, followed by the actual data, which is concluded by a 16-bit checksum which allows for error correction. The packet concludes with an ETX end character (e.g., 03h). Following reception of each packet, base station 14 sends a brief acknowledgment back to patient monitor 12, and if the packet contained any errors, patient monitor 12 will retransmit.

Figure 6:
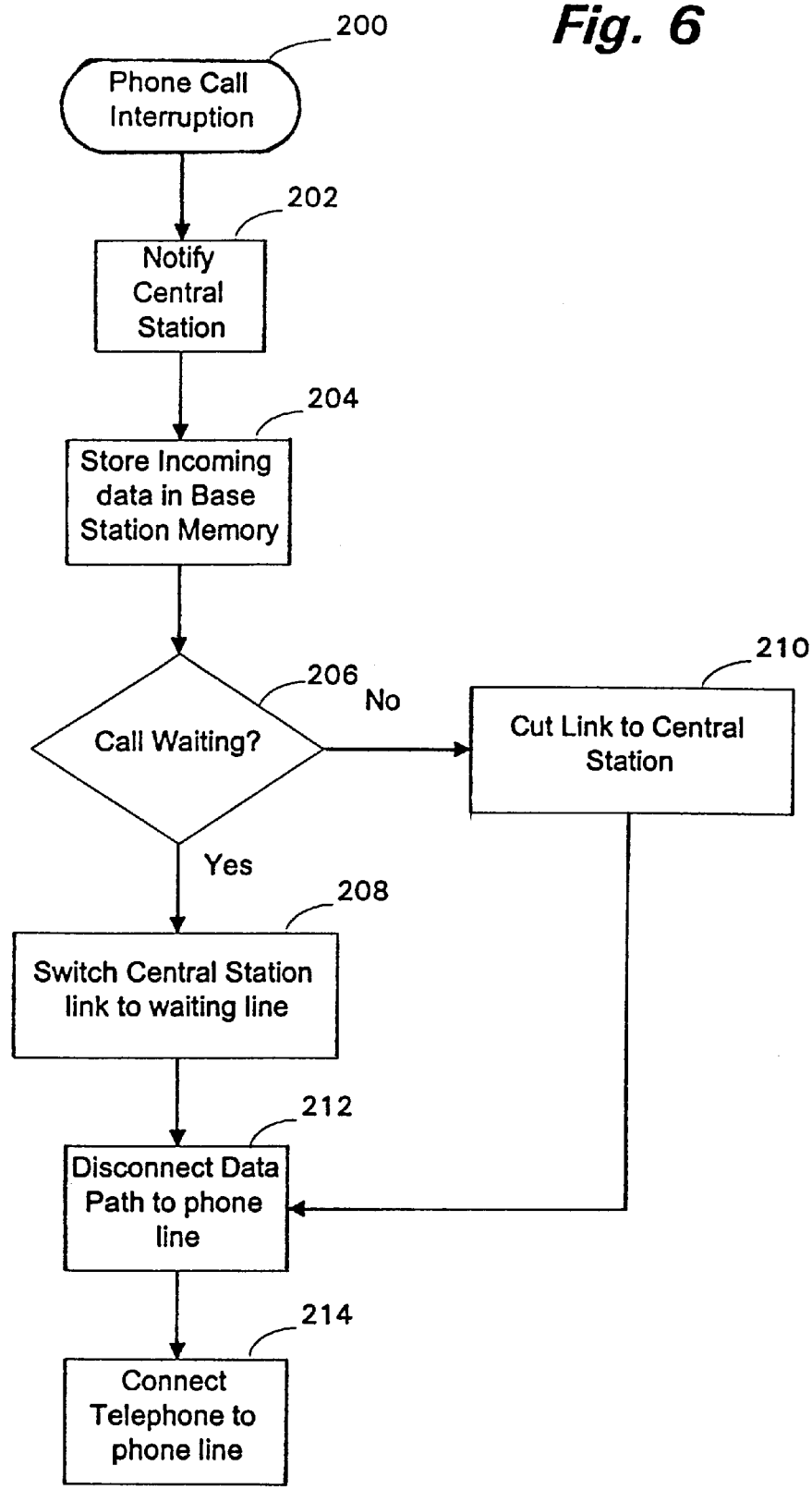
FIG. 6 is a flow chart of an interruption of data transmission by a telephone call.

Referring to FIG. 6, when a telephone call interrupts (step 200) normal data transmission between base station 14 and central station 16, base station 14 first notifies central station (202) of the interruption. At substantially the same time, base station 14 starts storing incoming data from patient monitor 12 in its local memory 56. If the telephone system provides for call waiting (step 206), then base station 14 switches the first line (with the link to central station 16) to be the waiting line (step 208). If there is not call waiting, the link to central station 16 is simply cut (step 210). Either way, the data path is disconnected to the phone line by signal switch 52 (step 212) and telephone 22 is instead connected to telephone network 20 (step 214).

Figure 7:
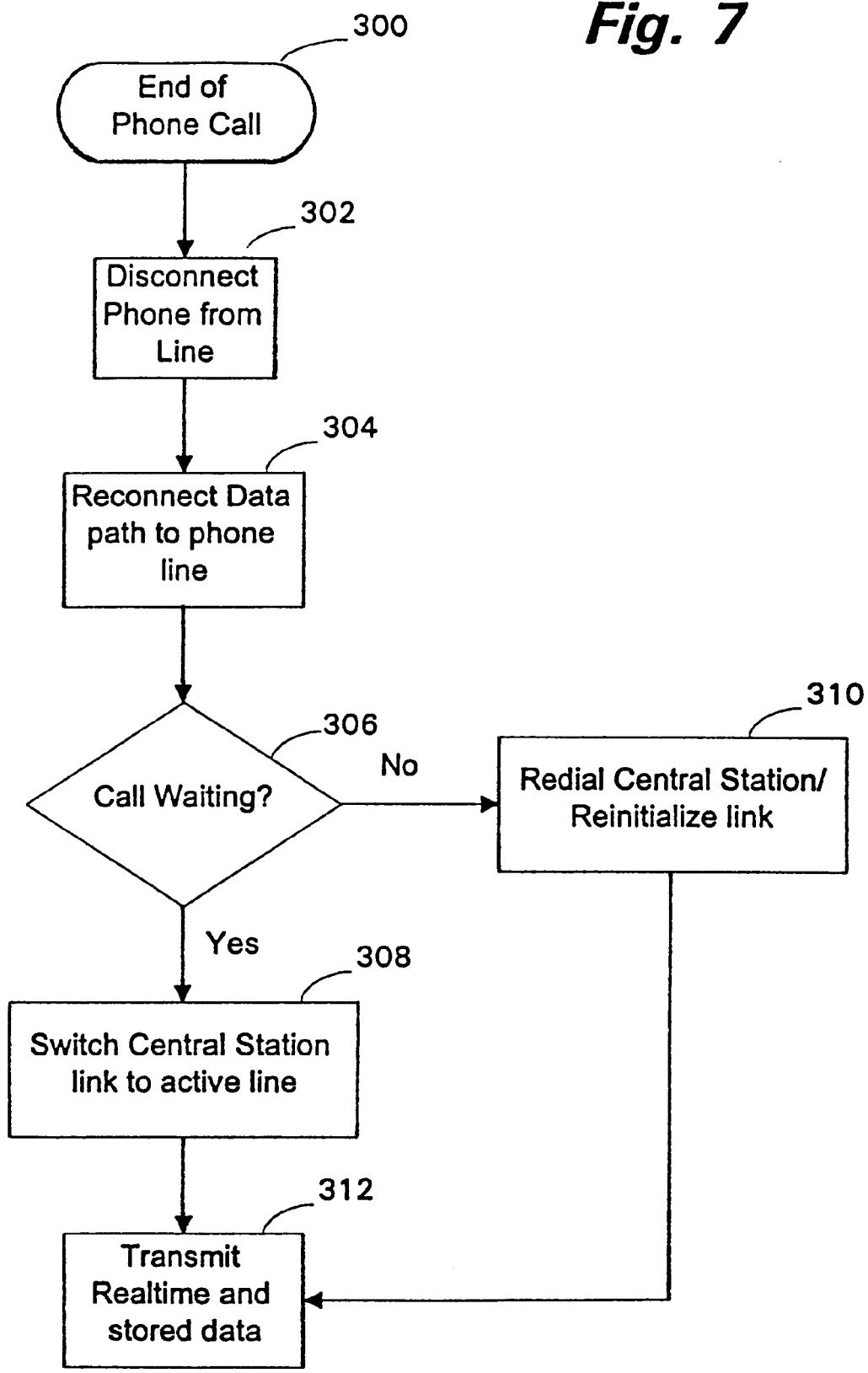
FIG. 7 is a flow chart of the resumption of data transmission after a telephone call.

Referring to FIG. 7, at the end of a telephone call (step 300), telephone 22 is disconnected from telephone network 20 by signal switch 52 (step 302). Then the data path (via modem 50) is reconnected to telephone network 20 (step 304). If the system has call waiting (step 306), then the waiting line attached to central station 16 is reestablished as the active line (step 308). If there is not call waiting, central station 16 is redialed and the link between base station 14 and central station 16 reestablished (step 310). Either way, base station 14 then begins to transmit both real-time data and stored data to central station 16 (step 312).

Figure 8:
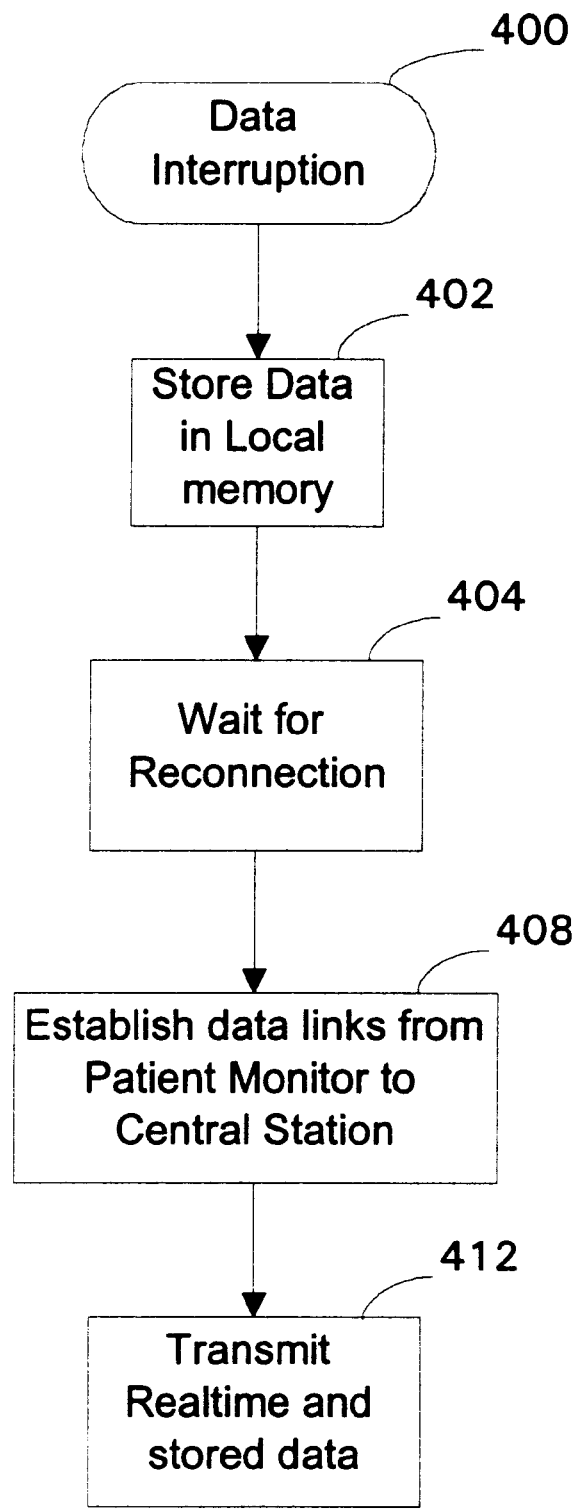
FIG. 8 is a flow chart of a data interruption procedure.

Referring to FIG. 8, regardless of whether a data interruption (step 400) occurs between patient monitor 12 and base station 14 (e.g., due to the patient leaving the reception area of base station 14), or between base station 14 and central station 16 (e.g., from line noise or other phone network interruptions), received data is stored locally up to the point of interruption (step 402). That is, if the interruption is between patient monitor 12 and base station 14, data is stored in the memory of patient monitor 12, and if the interruption is between base station 14 and central station 16, data is stored in the memory of base station 14. The system then waits for full data reconnection between patient monitor 12 and central station 16 (step 404). Once reconnection is performed, the system establishes the data links between patient monitor 12 and central station 16 (step 408). Once the data link is established, base station 14 transmits both real-time data and stored data to central station 16 (step 412).

Figure 9:
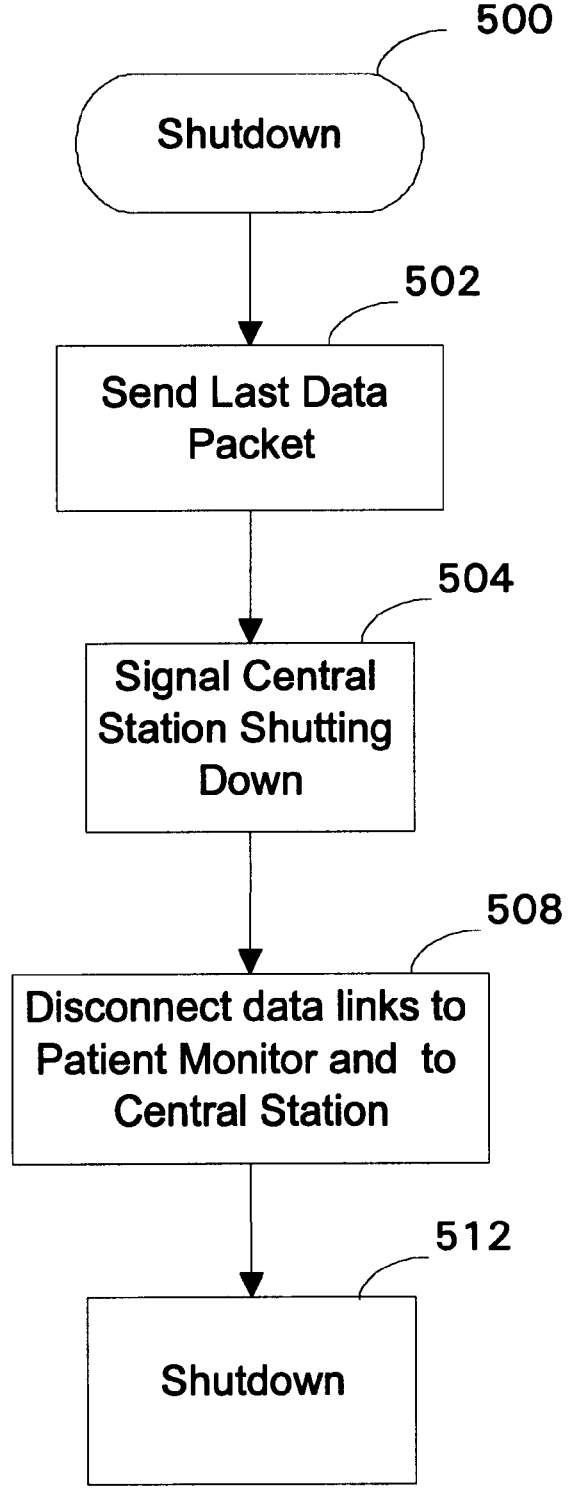
FIG. 9 is a flow chart of a shut down procedure

Referring to FIG. 9, when the system is to be shutdown (step 500), base station 14 sends the last data packet (step 502). Then base station 14 signals central station 16 that a shutdown is imminent (step 504) with a shutdown code (e.g., FFFFh), and disconnects data links to patient monitor 12 and central station 16 (step 508). At this point, the system including patient monitor 12 and base station 14 shuts down (step 510).

Other embodiments are within the scope of the claims. For example, a number of other forms of communications links between patient monitor and base station can be established, for example, through infrared communication links and other RF transceivers and protocols. The communication link between base station and central station can be through any number of communications channels, including private branch exchanges and local area networks. A variety of physiological data can be measured, stored, and sent by the patient monitor.

What is claimed is:

1. A physiological monitoring system comprising:
 a base station, the base station having a first wireless transceiver; and
 a patient monitor, the patient monitor comprising a data input, the data input configured to receive data regarding a physiological condition of a patient, the patient monitor further comprising a second wireless transceiver, the patient monitor capable of entering a wireless communications link with the base station through the first and second wireless transceivers, and of transmitting in substantially real-time the received data from the patient to the base station, the patient monitor further comprising a controller and a memory, the controller being configured to store in the memory the received data when the wireless communications link is interrupted.

2. The physiological monitoring system of claim 1 wherein the controller is further configured to end the storing of the received data and to send to the base station the stored received data from the memory of the patient monitor combined with new received data received through the data input, when the wireless communications link is reestablished.

3. The physiological monitoring system of claim 2 wherein the stored received data is combined with the new received data in an interleaved fashion.

4. The physiological monitoring system of claim 1 further comprising a central station coupled by a communications link to the base station.

5. The physiological monitoring system of claim 4 wherein the communications link is formed over a telephone network.

6. The physiological monitoring system of claim 4 wherein the base station further comprises a base station memory and a modem link.

7. The physiological monitoring system of claim 6 wherein the base station further comprises a base station controller, the base station controller configured to store in the base station memory received data from the patient monitor when the communications link with the central station is interrupted.

8. The physiological monitoring system of claim 7 wherein the base station controller is further configured to end the storing of the received data from the patient monitor and to send to the central station the stored received data from the base station memory combined with new received data received through the patient monitor, when the communications link is reestablished.

9. The physiological monitoring system of claim 8 wherein the stored received data is combined with the new received data from the patient monitor in an interleaved fashion.

10. The physiological monitoring system of claim 8 wherein the central station organizes the combined stored received data and the new received data into a substantially continuous, time ordered data record.

11. The physiological monitoring system of claim 7 wherein the communications link is interrupted when a telephone connected to the base station is used to make a telephone call.

12. The physiological monitoring system of claim 7 wherein the communications link is interrupted when a telephone connected to the base station receives an incoming telephone call.

13. The physiological monitoring system of claim 11 wherein the base station controller is further configured to end the storing of the received data from the patient monitor and to send to the central station the stored received data from the base station memory combined with new received data received through the patient monitor, when the telephone call ends.

14. The physiological monitoring system of claim 12 wherein the base station controller is further configured to end the storing of the received data from the patient monitor and to send to the central station the stored received data from the base station memory combined with new received data received through the patient monitor, when the telephone call ends.

15. A physiological monitoring system comprising:
a base station, the base station comprising a first wireless transceiver, a base station controller, and a base station memory; and
a patient monitor, the patient monitor comprising a data input, the data input configured to receive data regarding a physiological condition of a patient, the patient monitor further comprising a second wireless transceiver, the patient monitor capable of entering a wireless communications link with the base station through the first and second wireless transceivers, and of transmitting in substantially real-time the received data from the patient to the base station, the patient monitor further comprising a controller and a memory, the controller being configured to store in the memory the received data when the wireless communications link is interrupted, and to end the storing of the received data and to send to the base station the stored received data from the memory of the patient monitor combined with new received data received through the data input, when the wireless communications link is reestablished;
a central station coupled by a communications link to the base station, the base station controller configured to store in the base station memory received data from the patient monitor when the communications link with the central station is interrupted, and to end the storing of the received data from the patient monitor and to send to the central station the stored received data from the base station memory combined with new received data received through the patient monitor, when the communications link is reestablished, wherein the central station organizes the combined stored received data and the new received data into a substantially continuous, time ordered data record.

16. A method for physiological monitoring comprising:
receiving, at a patient monitor, data regarding a physiological condition of a patient,
transmitting in substantially real-time the received data from the patient to a base station via a wireless communications link, and
storing in memory of the patient monitor the received data when the wireless communications link is interrupted.

17. The method of claim 16 further comprising, when the wireless communications link is reestablished, ending the storing of the received data, and sending to the base station from the patient monitor memory the stored received data combined with new received data.

18. The method of claim 17 wherein the stored received data is combined with the new received data in an interleaved fashion.

19. The method of claim 16 further comprising sending the received data from the base station to a central station via a communications link.

20. The method of claim 19 wherein the communications link is formed over a telephone network.

21. The method of claim 19 further comprising storing in a memory at the base station received data from the patient monitor when the communications link with the central station is interrupted.

22. The method of claim 21 further comprising, when the communications link is reestablished, ending the storing of the received data from the patient monitor and sending to the central station the stored received data from the base station memory combined with new received data received through the patient monitor.

23. The method of claim 22 wherein the stored received data is combined with the new received data from the patient monitor in an interleaved fashion.

24. The method of claim 22 wherein the central station organizes the combined stored received data and the new received data into a substantially continuous, time ordered data record.

25. The method of claim 22 wherein the communications link is interrupted when a telephone connected to the base station is used to make a telephone call.

26. The method of claim 22 wherein the communications link is interrupted when a telephone connected to the base station receives an incoming telephone call.

27. The method of claim 25 further comprising, when the telephone call ends, ending the storing of the received data from the patient monitor and sending to the central station the stored received data from the base station memory combined with new received data received through the patient monitor.

28. The method of claim 26 further comprising, when the telephone call ends, ending the storing of the received data from the patient monitor and sending to the central station the stored received data from the base station memory combined with new received data received through the patient monitor.

29. A method for physiological monitoring comprising:

receiving, at a patient monitor, data regarding a physiological condition of a patient, transmitting in substantially real-time the received data from the patient to a base station via a wireless communications link, storing in memory of the patient monitor the received data when the wireless communications link is interrupted, and when the wireless communications link is reestablished, ending the storing of the received data, and sending to the base station from the patient monitor memory the stored received data combined with new received data, sending the received data from the base station to a central station via a communications link, storing in a memory at the base station received data from the patient monitor when the communications link with the central station is interrupted, and when the communications link is reestablished, ending the storing of the received data from the patient monitor and sending to the central station the stored received data from the base station memory combined with new received data received through the patient monitor, wherein the central station organizes the combined stored received data and the new received data into a substantially continuous, time ordered data record.

* * * * *